US010597683B2

(12) United States Patent
Lopes Ferreira et al.

(10) Patent No.: US 10,597,683 B2
(45) Date of Patent: Mar. 24, 2020

(54) IBE FERMENTATION METHOD

(71) Applicant: IFP Energies nouvelles, Rueil-Malmaison (FR)

(72) Inventors: Nicolas Lopes Ferreira, Croisilles (FR); Caroline Aymard, Lyons (FR); Remy Marchal, Chatou (FR); Frederic Monot, Nanterre (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 15/323,666

(22) PCT Filed: Jun. 29, 2015

(86) PCT No.: PCT/EP2015/064724
§ 371 (c)(1),
(2) Date: Jan. 3, 2017

(87) PCT Pub. No.: WO2016/001156
PCT Pub. Date: Jan. 7, 2016

(65) Prior Publication Data
US 2017/0137848 A1 May 18, 2017

(30) Foreign Application Priority Data
Jul. 1, 2014 (FR) ..................................... 14 56294

(51) Int. Cl.
| C12P 7/16 | (2006.01) |
| C10L 1/02 | (2006.01) |
| C12P 7/04 | (2006.01) |
| C12P 7/06 | (2006.01) |
| C12P 7/08 | (2006.01) |
| C12P 7/10 | (2006.01) |
| C12P 7/14 | (2006.01) |

(52) U.S. Cl.
CPC .................. *C12P 7/16* (2013.01); *C10L 1/02* (2013.01); *C12P 7/04* (2013.01); *C12P 7/065* (2013.01); *C12P 7/08* (2013.01); *C12P 7/10* (2013.01); *C12P 7/14* (2013.01); *C10L 2200/0469* (2013.01); *C10L 2290/26* (2013.01); *C12P 2201/00* (2013.01); *C12P 2203/00* (2013.01); *Y02E 50/10* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| 9,399,781 B2 | 7/2016 | Collas et al. |
| 9,453,245 B2 | 9/2016 | Ropars et al. |
| 2011/0207191 A1 | 8/2011 | Um et al. |
| 2014/0065683 A1 | 3/2014 | Ropars et al. |
| 2014/0322778 A1 | 10/2014 | Collas et al. |

FOREIGN PATENT DOCUMENTS

| FR | 2981089 A1 | 4/2013 |
| WO | 2012140334 A1 | 10/2012 |

OTHER PUBLICATIONS

Marchal et al. Conversion into acetone and butanol of lignocellulosic substrates by stem explosion., Biotechnology Letters (1986), 8(5): 365-370.*
International Search Report for PCT/EP2015/064724 dated Sep. 1, 2015.
Vrije, Truus de et al., "'In situ' removal of isopropanol, butanol and ethanol from fermentation broth by gas stripping," Bioresource Technology, 2013, vol. 137, pp. 153-159.
Collas, F. et al., "Simultaneous production of isopropanol, butanol, ethanol and 2,3-butanediol by Clostridium acetobutylicum ATCC 824 engineered strains," AMB Express, 2012, vol. 2, No. 45, 10 pages.
Jang, Yu-Sin "Metabolic Engineering of Clostridium acetobutylicum for the Enhanced Production of Isopropanol-Butanol-Ethanol Fuel Mixture," Biotechnol. Prog., vol. 29, No. 4, pp. 1083-1088.
Boonsombuti, Akarin et al., "Enhancement of ABE fermentation through regulation of ammonium acetate and D-xylose uptake from acid-pretreated corncobs," Ann Microbial, 2014, vol. 63, pp. 431-439.
Matta-El-Amouri, G. et al., "Mechanism of the acetone formation by Clostridium acetobutylicum," FEMS Microbiology Letters, 1985, vol. 30, pp. 11-16.
Matta-El-Ammouri, G. et al., "Effects of butyric and acetic acids on acetone-butanol formation by Clostridium acetobutylicum," Biochimie, 1987, vol. 69, pp. 109-115.
Kollaras, A. et al., "Adding Value to Sugarcane Basasse Using a Xylose Metabolising Yeast," Proc Aust Soc Sugar Cane Technol, 2011, vol. 33, 8 pages.

* cited by examiner

*Primary Examiner* — Iqbal H Chowdhury
(74) *Attorney, Agent, or Firm* — Millen, White, Zelano & Branigan, PC

(57) ABSTRACT

The present invention concerns a process for the production of an aqueous mixture comprising isopropanol, n-butanol and ethanol, comprising a step in which an aqueous solution containing C5 and/or C6 sugars and acetate is fermented under strict anaerobic conditions in the presence of a fermenting microorganism of the genus *Clostridium* and in which said aqueous solution has an acetate concentration in the range 0.5 to 10 g/L and a ratio by weight of (acetate)/(sum of C5 and/or C6 sugars) in the range 0.005 to 0.35 g/g.

16 Claims, 2 Drawing Sheets

IBE FERMENTATION METHOD

The present invention relates to a process for the production of an aqueous mixture comprising isopropanol, n-butanol and ethanol by fermentation of an aqueous solution comprising C5 and/or C6 sugars.

PRIOR ART

In order to meet the challenges of the changeovers in energy, a great deal of research is currently being carried out in order to develop processes for the "green" production of chemical intermediates which could provide a substitute for those generally obtained from oil.

Thus, for example, "green" ethylene can be synthesized by the dehydration of ethanol, which is itself obtained by the fermentation of sugars, preferably of glucose. In ethanol production processes which are termed "first generation" processes, the glucose which is fermented derives from sugar-containing plants such as beet or sugar cane. In what are known as "second generation" processes, the fermented sugars are obtained from lignocellulosic biomass, which represents one of the most abundant renewable sources in the world. "Second generation" processes generally employ the following steps:
  pre-treatment of biomass to render the cellulose and hemicellulose contained in the biomass accessible;
  enzymatic hydrolysis of the cellulose and hemicellulose in order to produce a hydrolysate containing glucose;
  fermentation of the glucose contained in the hydrolysate into ethanol; and
  separation/purification of the ethanol obtained after fermentation.

Another example of the process which is currently being studied concerns the "butyl" fermentation of sugars that can be used for the production of solvents. Examples that may be cited are "ABE" fermentations, which correspond to the production of a mixture comprising acetone, n-butanol (major product) and ethanol, or "IBE", which produces a mixture containing isopropanol, n-butanol and ethanol. These fermentations are carried out under anaerobic conditions and in the presence of a fermenting microorganism of the genus *Clostridium*.

These types of alcohol and/or solvent production processes are difficult to validate economically, even for operators with large mobilisable resources. Optimizing these types of processes is primarily directed at improving the yield of the step for fermentation of the sugars by the best adapted microorganisms.

One aim of the invention is to propose a process for the production of an aqueous mixture (isopropanol, n-butanol, ethanol) by fermentation of an aqueous solution of sugars containing 5 (C5) and/or 6 (C6) carbon atoms by means of a fermenting microorganism wherein the solvent yield is improved.

SUMMARY OF THE INVENTION

Thus, the invention concerns a process for the production of an aqueous mixture comprising isopropanol, n-butanol and ethanol, comprising a step in which an aqueous solution containing C5 and/or C6 sugars and acetate is fermented under anaerobic conditions in the presence of a fermenting microorganism of the genus *Clostridium* and in which said aqueous solution has an acetate concentration in the range 0.5 to 10 g/L and a ratio by weight of (acetate)/(sum of C5 and/or C6 sugars) in the range 0.005 to 0.35 g/g.

Surprisingly, the inventors have established that the presence of acetate in an aqueous solution of C5 and/or C6 sugars means that the "IBE" fermentation performances for the fermenting microorganism of the genus *Clostridium* can be improved, and in particular the concentration of isopropanol and n-butanol in the aqueous solution obtained from the fermentation can be increased.

In the context of the invention, the term "acetate" denotes the deprotonated form of acetic acid, i.e. with chemical formula $CH_3COO^-$. The proportion of acetate with respect to acetic acid and its concentration in the aqueous solution may be adjusted by means of the "pH" variable of said solution.

Preferably, the concentration of acetate in the aqueous solution is in the range 1 to 8 g/L. More preferably, the concentration of acetate in the aqueous solution is in the range 2 to 6 g/L, preferably in the range 3 to 6 g/L.

Preferably, the pH of the aqueous solution containing C5 and/or C6 sugars and acetate is in the range 4 to 8. More preferably, the pH of the aqueous solution containing C5 and/or C6 sugars and acetate is in the range 5 to 8.

Preferably, the ratio by weight of (acetate)/(sum of the C5 and/or C6 sugars) is in the range 0.08 to 0.35 g/g. More preferably, the ratio by weight of (acetate)/(sum of the C5 and/or C6 sugars) is in the range 0.09 to 0.2 g/g.

Preferably, the concentration of C5 and/or C6 sugars in the aqueous solution is in the range 30 to 100 g/L.

In accordance with one embodiment, the aqueous solution containing C5 and/or C6 sugars and acetate is a residual stream obtained from a step for the pre-treatment of a lignocellulosic biomass.

In accordance with another embodiment, the aqueous solution containing C5 and/or C6 sugars and acetate is a stillage produced by the fermentation of sugars. Optionally, the stillage may have been concentrated, for example by evaporation.

Alternatively, the aqueous solution containing C5 and/or C6 sugars and acetate is a hydrolysate obtained from enzymatic hydrolysis of a lignocellulosic biomass.

In accordance with another aspect of the invention, the aqueous solution containing C5 and/or C6 sugars and acetate is an aqueous solution containing C5 and/or C6 sugars supplemented with an aqueous solution containing acetate which is selected from:
  a stillage produced by fermentation of sugars;
  a hydrolysate obtained by enzymatic hydrolysis of a lignocellulosic biomass;
  a residual effluent obtained from a step for pre-treatment of a lignocellulosic biomass.

Preferably, the C5 sugar is xylose and the C6 sugar is glucose.

The glucose may optionally derive from a stream obtained from the step for enzymatic hydrolysis of a first generation process for the production of biofuel (for example ethanol) using sugar-containing plants as the starting material such as, for example, sugar beet and sugar cane, or indeed corn or grains of wheat.

Preferably, the fermenting microorganism used in the process in accordance with the invention is selected from the strains *Clostridium acetobutylicum* and *Clostridium beijerinckii*.

"IBE" fermentations are carried out at a temperature which is generally in the range 30° C. to 37° C., preferably at 34° C., for a period in the range 30 to 120 hours and by maintaining continuous stirring in order to homogenize the culture medium. Preferably, the fermentation is carried out in a batch or fed-batch mode, as is well known to the person skilled in the art.

The invention also concerns a process for the production of biofuel starting from lignocellulosic biomass, comprising the following steps:
pre-treating the lignocellulosic biomass in order to render the cellulose and hemicellulose contained in the biomass accessible;
carrying out an enzymatic hydrolysis on the cellulose and hemicellulose in order to produce a hydrolysate containing sugars;
fermenting the sugars of the hydrolysate in the presence of a fermenting microorganism in order to produce a biofuel,
characterized in that the process furthermore carries out a process for the production of an aqueous mixture comprising isopropanol, n-butanol and ethanol by fermentation of an aqueous solution containing C5 and/or C6 sugars and acetate, said solution being selected from:
a residual effluent obtained from the step for pre-treatment of the lignocellulosic biomass;
a stillage produced by fermentation of the sugars;
the hydrolysate obtained from enzymatic hydrolysis.

Thus, the process for the production of the "IBE" mixture in accordance with the invention is advantageously integrated into a second generation process for the production of alcohol and/or solvents in a manner such as to treat and upgrade the by-products generated, in particular during the pre-treatment and fermentation step.

DETAILED DESCRIPTION OF THE INVENTION

The invention pertains to a fermentation process termed "IBE" in order to produce, with the aid of a microorganism of the genus *Clostridium*, a mixture of solvents (isopropanol, n-butanol, ethanol) from an aqueous solution containing C5 and/or C6 sugars and in the presence of acetate. The fermentation is operated in the absence of oxygen and in a bioreactor also known by the term "fermenter". The bioreactor is a piece of equipment for propagating fermenting microorganisms which are capable of producing molecules (solvents or other organic compounds) of interest. Bioreactor fermentation can thus be used to proliferate a microorganism in batch mode with control of the key parameters such as pH, stirring and the temperature of the medium.

The fermentation step consists of causing the microorganisms to develop and to recover a reaction effluent or fermentation must containing an aqueous solution of the mixture (isopropanol, n-butanol, ethanol). The product from the fermentation is then generally treated in a concentration step in order to provide an aqueous solution (isopropanol, n-butanol, ethanol) which is concentrated.

The fermentation is carried out at a temperature which is generally in the range 30° C. to 37° C., preferably at 34° C., for a period in the range 30 to 120 hours and by continuously stirring in order to homogenize the reaction medium.

In accordance with the invention, the aqueous solution generally contains C5 and/or C6 sugars in a concentration of 30 to 100 g/L, and also acetic acid in the deprotonated form, i.e. in the form of an acetate with formula $CH_3COO^-$. The concentration of acetate in said aqueous solution is in the range 0.5 to 10 g/L, preferably in the range 1 to 8 g/L, more preferably in the range 2 to 6 g/L and highly preferably in the range 3 to 6 g/L. Furthermore, the ratio by weight of (acetate)/(sum of C5 and/or C6 sugars) is in the range 0.005 to 0.35. In accordance with a highly preferred embodiment, the ratio by weight of (acetate)/(sum of C5 and/or C6 sugars) is in the range 0.08 to 0.35 g/g, preferably in the range 0.09 to 0.2.

The presence of acetic acid (a weak carboxylic acid with a pKa equal to 4.8 at 25° C.) in the acetate form depends on the pH of the aqueous solution. Thus, in accordance with the invention, the aqueous solution has a pH in the range 4 to 8, preferably in the range 5 to 8. In the context of the invention, the acetate may be added to an aqueous solution of C5 and/or C6 sugars in order to satisfy the concentration of acetate in the culture medium.

The process in accordance with the invention involves the use of a microorganism of the genus *Clostridium*, which is a bacterium from the anaerobic gram-positive bacillae family. Preferably, the fermenting microorganism is selected from the strains *Clostridium acetobutylicum* and *Clostridium beijerinckii* and may be either a natural strain or a strain which has been genetically modified in order to produce isopropanol.

The concentration of microorganism in the fermentation medium is generally in the range 1 to 30 g/L, preferably in the range 2 to 10 g/L.

The aqueous solution of C5 and/or C6 sugars which may be fermented by the process in accordance with the invention may have a variety of origins. However, in order to solve the problem of producing solvents in a "green" manner, the aqueous solution advantageously originates from treatment of a renewable resource. Preferably, the renewable resource is of the lignocellulosic biomass type, which in particular comprises woody substrates (hardwood and softwood), agricultural by-products (straw) or those from industries generating lignocellulosic waste (agroalimentary, paper industries).

The aqueous solution of C5 and/or C6 sugars may also be obtained from sugar-containing plants such as sugar beet and sugar cane, for example, or indeed from corn or from grains of wheat.

Any C5 sugar which is naturally present in the various lignocellulosic biomasses (mono- or dicotyledonous) used for the production of biofuel by a biological pathway may be fermented by the process in accordance with the invention. Preferably, the C5 sugars are selected from xylose and arabinose.

Any C6 sugar may also be fermented by the process in accordance with the invention. Preferably, the C6 sugars are selected from glucose, mannose and galactose. More preferably, the C6 sugar is glucose.

The aqueous solution of C5 and/or C6 sugars may be obtained from a step of a second generation process for the production of alcohol and/or solvents. In this case, the solution may be an effluent originating from a step for the pre-treatment of lignocellulosic biomass. The pre-treatment step, which is intended to modify the physical and physicochemical properties of the lignocellulosic material with a view to improving the accessibility to the cellulose trapped in the lignin and hemicellulose matrix, generates residual effluents generally containing a mixture of C5 and/or C6 sugars which may then advantageously be used for the IBE fermentation in accordance with the invention. As an example, the residual effluent may be obtained from a pre-treatment selected from acid cooking, alkaline cooking, steam explosion with or without acid impregnation, and from Organosolv processes. An effluent of this type obtained from pre-treatment is advantageous because it contains sugars which are useful for fermentation, as well as acetic acid (or acetate).

Preferably, the aqueous solution containing C5 and/or C6 sugars and acetate is a residual effluent obtained from a pre-treatment by steam explosion. As well as "steam explosion", this pre-treatment is also known as "steam gunning", "explosive decompression", or "steam pre-treatment". In this process, the biomass is heated rapidly to high temperature (150° C.-250° C.) by injecting steam under pressure. The treatment is generally stopped by sudden decompression, known as decompression or explosion, which destroys the structure of the lignocellulosic matrix. The residence time varies from 10 seconds to a few minutes for this type of pre-treatment for pressures of 10 to 50 bar. Many configurations are possible for this type of pre-treatment. It may be carried out in batch mode, or continuously. Steam explosion may be preceded by an acid impregnation in order to favour hydrolysis of the hemicelluloses during cooking. When steam explosion is applied to a pre-acidified substrate, for example pre-acidified with $H_2SO_4$, it generally results in dissolution and almost complete hydrolysis of the hemicelluloses into their monomers. Using an acid pre-impregnation in particular enables the temperature of the process to be reduced (between 150° C. and 200° C., as opposed to 250° C. for steam explosion without acid impregnation) and thus minimizes the formation of degradation compounds.

Thus, the aqueous stream containing C5 and/or C6 sugars and acetate which is fermented by the process in accordance with the invention may originate from an acid liquor recovered from the end of the step for acid impregnation of a lignocellulosic biomass which precedes the step for pre-treatment by steam explosion.

It is also possible to use the liquid fraction recovered after an operation for solid/liquid separation carried out on the pre-treated substrate obtained after the decompression phase of the step for pre-treatment by steam explosion as the source of the aqueous solution containing C5 and/or C6 sugars and acetate.

It is also possible to use a hydrolysate obtained by enzymatic hydrolysis of the cellulose and hemicellulose liberated during the step for pre-treatment of the biomass as the aqueous solution of C5 and/or C6 sugars and acetate. By way of example, the hydrolysis may be carried out in the presence of cellulolytic and/or hemicellulolytic enzymes produced by a microorganism from the genuses *Trichoderma, Aspergillus, Penicillium* or *Schizophyllum*.

In the context of the invention, the aqueous solution of C5 and/or C6 sugars and acetate may also be a residual effluent obtained from the fermentation step which is also denoted by the term "stillage". Typically, this liquid residue from fermentation contains non-fermented sugars including pentoses (C5 sugars) and even traces of hexoses which are the most difficult to metabolize with the fermenting microorganism (for example galactose).

In order to keep to the acetate content in the aqueous solution of sugars, it is of course possible to enrich said aqueous solution of C5 and/or C6 sugars and acetate by supplying the medium with supplemental acetic acid. Advantageously, the following sources are used as the acetate source:

the acidic liquor recovered from the end of the step for acid impregnation of a lignocellulosic biomass which precedes the steam explosion step, the liquid fraction obtained from an operation for solid/liquid separation carried out on the pre-treated biomass which is recovered after the decompression phase of the step for pre-treatment by steam explosion;

a condensate obtained from treatment of the steam phase generated by the step for pre-treatment by steam explosion.

BRIEF DESCRIPTION OF THE FIGURES

Exemplary embodiments of the process in accordance with the invention will be described below with reference to the drawings in which:

FIG. 1 represents an exemplary embodiment of the process in accordance with the invention which is advantageously integrated into a second generation process for the production of alcohol and/or solvents.

The substrate (lignocellulosic biomass) is introduced into the pre-treatment reactor 2 via the line 1. The reagents and utilities such as the steam required to carry out the pre-treatment are introduced via the line 3. A pre-treated substrate is extracted from the pre-treatment reactor 2 via the line 6 and a residual pre-treatment effluent is evacuated therefrom via the line 4. The composition of the residual effluent depends on the method used for the pre-treatment. When the pre-treatment is acidic in type with or without steam explosion, the residual effluent may contain between 0.5 and 10 g/L of acetic acid.

In the context of the invention, the residual effluent from the pre-treatment, containing C5 and/or C6 sugars and acetate, is advantageously treated using the process in accordance with the invention after optional adjustment of the pH of the residual effluent when its pH is outside the range of 4 to 8 pH units.

Figure 1:
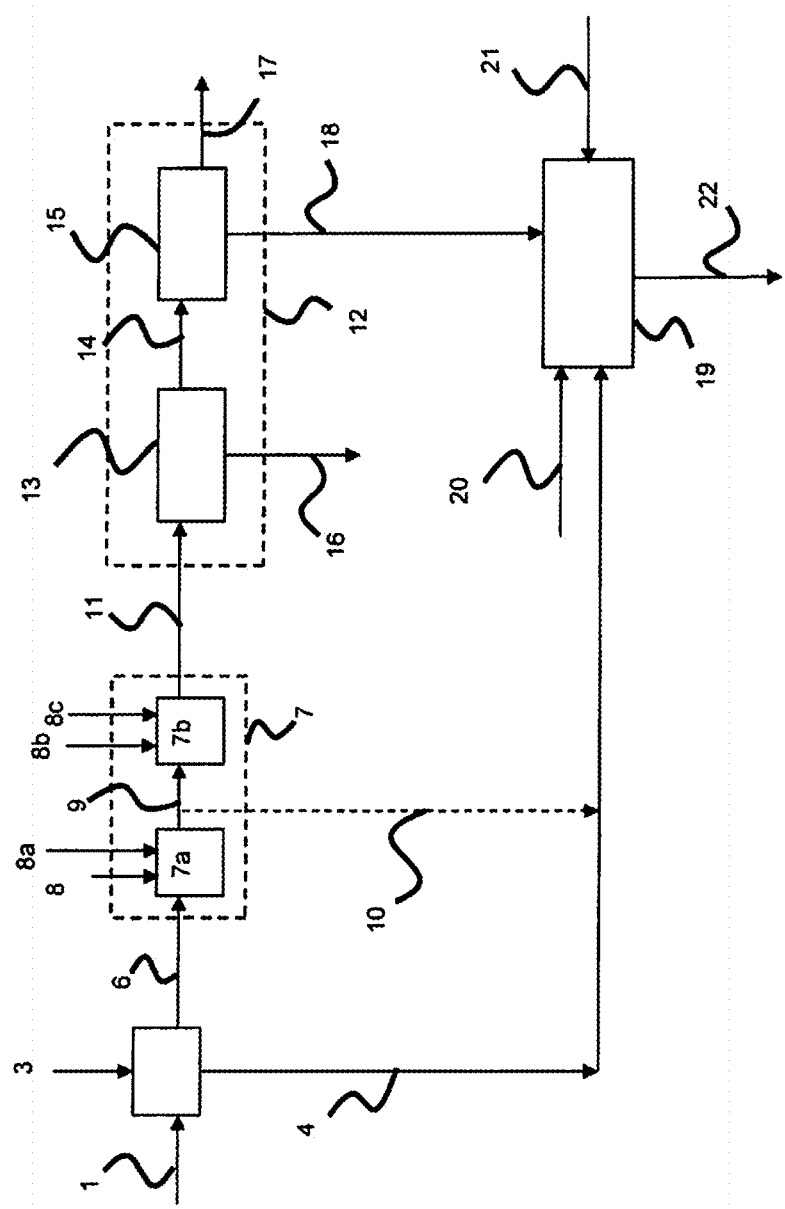
FIG. 1 is a layout of a second generation process for the production of alcohol and/or solvents integrating an "IBE" fermentation unit.

As indicated in FIG. 1, the residual effluent is sent to the "IBE" fermentation reactor 19 via the line 4 in order to produce an aqueous solution containing an (isopropanol, n-butanol, ethanol) mixture.

Regarding the pre-treated substrate, this is sent to a unit 7 for converting the cellulose into alcohol and/or solvent via the line 5. As can be seen in FIG. 1, the conversion unit 7 comprises at least one reactor 7a for enzymatic hydrolysis of the cellulose into hexoses (preferably glucose) and a bioreactor for alcoholic and/or solvent fermentation 7b, which transforms the hexoses into alcohol and/or solvents. Preferably, the fermentation is of the ethyl type which produces ethanol.

The enzymatic hydrolysis conditions, principally the quantity of dry matter of the mixture to be hydrolysed and the quantity of enzymes used, are selected in a manner such as to dissolve in the range 20% to 99% of the cellulose in the reactor 7a, and more preferably in the range 30% to 95%. The water necessary to obtain the envisaged solid matter content is added via the conduit 8. The cellulolytic and/or hemicellulolytic enzymes are added via the line 8a. The hydrolysate obtained from the outlet from the reactor 7a is sent to the fermentation bioreactor 7b via the line 9. In accordance with a variation, the steps 7a and 7b are carried out at the same time in the same reactor.

The microorganisms used for fermentation of the hexoses which are liberated are introduced via the line 8b, and the additives required to adjust the pH or for liquefaction are introduced into the bioreactor 7b via the line 8c.

A fermentation must containing an aqueous mixture of alcohol and/or solvents and solid matter (principally lignin) is withdrawn from the bioreactor 7b via the line 11 and sent to a treatment unit 12 to recover a concentrated aqueous solution of alcohol and/or solvents.

As indicated in FIG. 1, the treatment unit 12 comprises a unit for concentrating the alcohols and/or solvents 13 and a solid/liquid separation unit 15. At the end of the concentration step, a concentrated aqueous stream of alcohol and/or solvents is recovered which is evacuated via the line 16, along with a sludge which is withdrawn via the line 14. The sludge is composed of a solid fraction essentially constituted by cellulose, hemicellulose and lignin which has not been hydrolysed, and a liquid fraction denoted by the term "stillage". As indicated in FIG. 1, the sludge is treated in the solid/liquid separation unit 15. This unit 15 can be used to separate the residual solids via the line 17 and a liquid fraction (or stillage) via the line 18.

The stillage, which is an aqueous solution containing non-fermented sugars, in particular containing pentoses (xylose, arabinose) and even traces of hexoses (for example galactose, which is the hexose which is the most difficult to metabolize by conventional yeasts), as well as oligomers of sugars and the acetate, thus constitutes a useful solution for the "IBE" fermentation in accordance with the invention.

As can be seen in FIG. 1, the stillage is advantageously treated in the "IBE" fermentation reactor 19. Alternatively, the stillage may be pre-concentrated before being sent to the reactor 19.

In accordance with another option, the sludge may be sent directly to the "IBE" bioreactor 19. The "IBE" fermentation bioreactor 19 is supplied with microorganisms of the genus *Clostridium* via the line 21 and with acetic acid via the line 20. The presence of the line 20 supplying acetic acid is useful when the culture medium in the reactor 19 does not contain sufficient acetate as required by the invention.

It should be noted that the added acetic acid may originate from a condensate produced by the pre-treatment step when it involves a steam explosion.

An aqueous "IBE" mixture is thus recovered from the outlet from the bioreactor 19 via the line 22. As can be seen in FIG. 1, it is also possible to provide for the line 9 to be tapped by the line 10 in order to supply the bioreactor 19 with hydrolysate produced by the enzymatic hydrolysis reactor 7a. The presence of the line 10 in particular means that the concentration of C5 and/or C6 sugars in the culture medium in the bioreactor 19 can be regulated.

Figure 2:
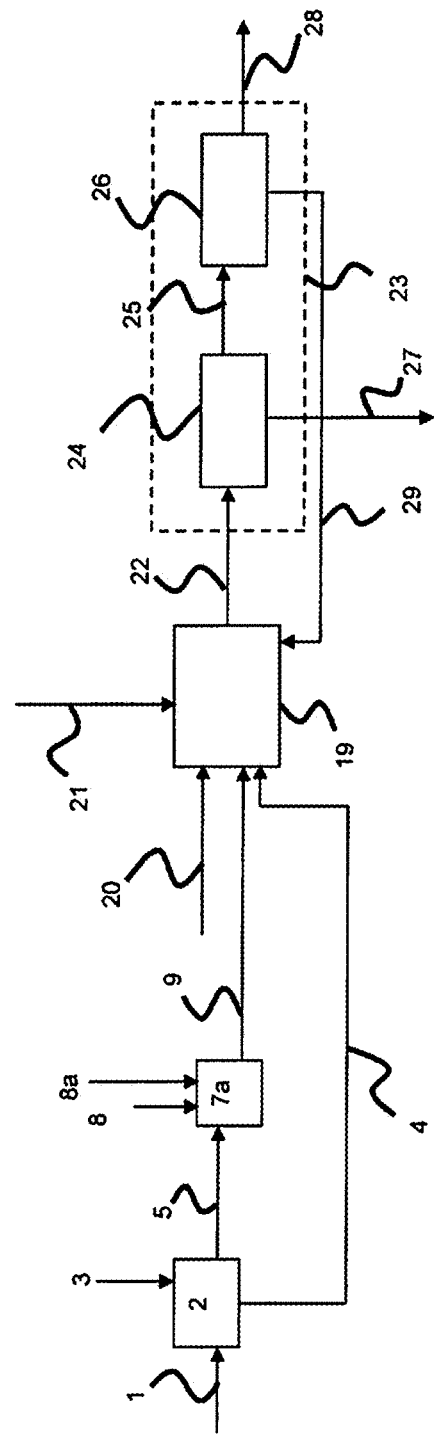
FIG. 2 is a layout of the "IBE" fermentation process in accordance with the invention.

FIG. 2 represents an exemplary embodiment of the process for the production of an aqueous mixture of isopropanol, n-butanol and ethanol in accordance with the invention.

The substrate (lignocellulosic biomass) is introduced into the pre-treatment reactor 2 via the line 1. The reagents and utilities such as the steam necessary to carry out the pre-treatment are introduced via the line 3. A pre-treated substrate is extracted from the pre-treatment reactor 2 via the line 5 and a residual pre-treated effluent is evacuated via the line 4. The composition of the residual effluent depends on the method used for the pre-treatment.

In this embodiment, the residual pre-treatment effluent containing C5 and/or C6 sugars and acetate is advantageously treated by means of the process in accordance with the invention. As indicated in FIG. 2, the residual effluent is sent to the "IBE" fermentation reactor 19 via the line 4 in order to produce an aqueous solution containing an aqueous mixture of isopropanol, n-butanol and ethanol.

Regarding the pre-treated substrate, this is sent via the line 5 to a unit for converting the cellulose into hexoses 7a, in which enzymatic hydrolysis of the cellulose is carried out. The conditions for enzymatic hydrolysis, principally the dry matter content of the mixture to be hydrolysed and the quantity of enzymes used, are selected in a manner such that in the range 10% to 99% of the cellulose is dissolved in the reactor 7, and more particularly in the range 15% to 95%. The water necessary for obtaining the envisaged solid matter content is added via the conduit 8. The cellulolytic and/or hemicellulolytic enzymes are added via the line 8a.

The hydrolysate obtained from the outlet from the cellulose conversion unit 7a is sent to the "IBE" fermentation reactor 19 via the line 9.

Microorganisms of the genus *Clostridium* used for the fermentation of the hexoses and pentoses are introduced via the line 21.

A fermentation must containing an aqueous mixture of isopropanol, n-butanol, ethanol and the solid matter (principally lignin) is then withdrawn from the bioreactor 19 via the line 22 and sent to a treatment unit 23 in order to recover a concentrated aqueous solution of isopropanol, n-butanol and ethanol.

As indicated in FIG. 2, the treatment unit 23 comprises a unit 24 for concentrating solvents and a solid/liquid separation unit 26. At the end of the concentration step, a concentrated aqueous stream of solvents is recovered and evacuated via the line 27 along with a sludge which is withdrawn via the line 25. The sludge is composed of a solid fraction essentially constituted by cellulose, hemicellulose and lignin which have not been hydrolysed, and a liquid fraction denoted by the term "stillage". The sludge is thus treated inside the solid/liquid separation unit 26. This unit 26 can be used to separate the residual solids via the line 28 and a liquid fraction (or stillage) via the line 29.

The stillage, which is an aqueous solution containing residual sugars and possibly acetate, constitutes a useful solution for IBE fermentation. As can be seen in FIG. 2, the stillage is advantageously recycled to the "IBE" fermentation bioreactor 19 via the line 29. Alternatively, the sludge, containing the solid residues and stillage, is sent directly to the "IBE" bioreactor 19. The "IBE" fermentation reactor is supplied with acetic acid (or acetate) via the line 20 when the culture medium in the reactor 19 does not contain sufficient acetate as required by the invention. The acetic acid (or acetate) may optionally originate from a condensate produced after treatment of the steam phase produced by the decompression phase of the steam explosion pre-treatment.

EXAMPLE

A batch isopropanol/butanol/ethanol fermentation was carried out using the *Clostridium beijerinckii* NRRL B593 (DSMZ 6423) strain and in a CM1 culture medium containing 60 g/L of glucose to which 0 g/L or 3 g/L or 6 g/L of ammonium acetate had been added.

The composition for 1 litre of CM1 solution is detailed below:

|  | Quantity [g] |
| --- | --- |
| Yeast extract | 5.00 |
| $KH_2PO_4$ | 1.00 |
| $K_2HPO_4$ | 0.60 |
| $CH_3COONH_4$ | 2.90 |
| $FeSO_4 \cdot 7H_2O$ | 0.50 |
| $MgSO4 \cdot 7H_2O$ | 1.00 |
| p-amino-benzoate | 0.10 |
| Glucose | 60 |

The fermentation was carried out batchwise under the following operating conditions:
- temperature of 34° C.
- stirring at 150 rpm.

It should be noted that the pH was not regulated in fermentation media containing acetate.

The quantity of the *Clostridium beijerinckii* NRRL B593 strain employed for the tests was in the range 16 to 24 g/L and was determined by measuring the optical density at 600 nm of the culture medium after seeding the strain.

Table 1 provides the final concentrations of substrates and products obtained following batch culture after 50 hours.

TABLE 1

|  | Control $pH_0 = 5.8$ | Ac1 No regulation of pH | Ac2 No regulation of pH |
|---|---|---|---|
| Added acetate | 0 g/L | 3.0 g/L | 6 g/L |
| Concentration of acetate | 2.9 | 5.9 | 8.9 |
| Weight ratio [acetate/glucose] (g/g) | 0.048 | 0.098 | 0.148 |
| Glucose consumption [g/L] | 36.5 | 36.8 +/− 1.7 | 38.7 |
| Acetic acid [1] [g/L] | 0.8 | −1.7 +/− 0.01 | −3.3 |
| Butyric acid [g/L] | 0.1 | 0.3 +/− 0.1 | 1.8 |
| Ethanol [g/L] | 0.1 | 0.1 +/− 0.01 | 0.2 |
| Isopropanol [g/L] | 2.9 | 4.5 +/− 0.3 | 5.9 |
| Butanol [g/L] | 5.6 | 8.4 +/− 1.9 | 8.2 |
| Total solvents [g/L] | 8.9 | 13.2 +/− 2.3 | 16.6 |

[1] a negative value indicated a net consumption of acetic acid ([acetic acid]$_{final}$ − [acetic acid]$_{initial}$)

Monitoring the pH of the fermentation medium indicated that the pH rose to 5.3 in the media containing acetate without having an impact on the performances of the strain. This change in the pH in bioreactors may be the consequence of numerous equilibria between production and re-assimilation of the acids.

Thus, it was observed that the strain, irrespective of the culture medium (containing or not containing acetate), consumed the same quantities of glucose after 50 hours of fermentation. In contrast, the production of solvents (isopropanol and butanol) greatly increased when 3 g/L of acetate had been added to the culture medium (i.e. a ratio by weight of (acetate)/(sum of C5 and/or C6 sugars) of 0.098) or 6 g/L of acetate (i.e. a ratio by weight of (acetate)/(sum of C5 and/or C6 sugars) of 0.148).

Consumption of acetate was also observed, of 1.8 or 3.3 g/L, for fermentations in media respectively containing 3 or 6 g/L of acetate, by the *Clostridium beijerinckii* NRRL B593 strain.

The invention claimed is:

1. A process for the production of an aqueous mixture comprising isopropanol, n-butanol and ethanol, comprising fermenting an aqueous culture medium containing C5 and/or C6 sugars and acetate under anaerobic conditions in the presence of *Clostridium beijerinckii*, wherein said aqueous culture medium has an acetate concentration in the range 2 to 10 g/L and a ratio by weight of (acetate)/(sum of C5 and C6 sugars) in the range 0.098 to 0.35 g/g.

2. The process of claim 1, wherein the concentration of acetate in the aqueous culture medium is in the range 2 to 8 g/L.

3. The process of claim 2, wherein the concentration of acetate is in the range 2 to 6 g/L.

4. The process of claim 1, wherein the pH of the aqueous culture medium containing C5 and/or C6 sugars and acetate is in the range 4 to 8.

5. The process of claim 1, wherein the aqueous culture medium comprises C5 and/or C6 sugars and acetate is obtained from pre-treatment of a lignocellulosic biomass.

6. The process of claim 5, wherein the aqueous culture medium comprises C5 and/or C6 sugars and acetate is obtained from a pre-treatment by steam explosion.

7. The process of claim 1, wherein the aqueous culture medium containing C5 and/or C6 sugars and acetate comprises a stillage produced by the fermentation of sugars.

8. The process of claim 1, wherein the aqueous culture medium containing C5 and/or C6 sugars and acetate comprises a hydrolysate obtained from enzymatic hydrolysis of a lignocellulosic biomass.

9. The process of claim 1, wherein the aqueous culture medium supplemented with an aqueous solution containing acetate which is:
- a residual effluent obtained from a step for pre-treatment of a lignocellulosic biomass;
- a stillage produced by fermentation of sugars; or
- a hydrolysate obtained by enzymatic hydrolysis of a lignocellulosic biomass.

10. The process of claim 1, wherein the C5 sugar is xylose and the C6 sugar is glucose.

11. The process of claim 1, wherein the concentration of C5 and/or C6 sugars in the aqueous culture medium is in the range 30 to 100 g/L.

12. The process of claim 1, wherein the concentration of fermenting microorganism of the genus *Clostridium* in the aqueous culture medium is in the range 1 to 30 g/L.

13. The process of claim 1, wherein the fermentation is carried out at a temperature in the range 30° C. to 37° C., maintaining continuous stirring.

14. The process of claim 1, wherein the aqueous culture medium is supplemented with a byproduct of a process for the production of biofuel starting from lignocellulosic biomass, said biofuel production process comprising:
- pre-treating the lignocellulosic biomass in order to render the cellulose and hemicellulose contained in the biomass accessible;
- carrying out an enzymatic hydrolysis on the cellulose and hemicellulose in order to produce a hydrolysate containing sugars; and
- fermenting the sugars of the hydrolysate in the presence of a fermenting microorganism in order to produce a biofuel, wherein acetate is coproduced as a byproduct of the process.

15. The process of claim 14, wherein the byproduct of the biofuel production process comprises acetate at a higher concentration than the culture medium, whereby the acetate concentration of the culture medium is increased after the culture medium is supplemented with the byproduct of the biofuel production process, as compared to the acetate concentration of the culture medium prior to supplementation.

16. The process of claim 1, wherein at least a portion of the acetate in the aqueous culture medium is obtained from:
(a) pre-treatment of a lignocellulosic biomass, optionally wherein the pre-treatment is steam explosion;
(b) a stillage produced by the fermentation of sugars; or
(c) a process for the production of biofuel starting from lignocellulosic biomass, said biofuel production process comprising:
- pre-treating the lignocellulosic biomass in order to render the cellulose and hemicellulose contained in the biomass accessible;

carrying out an enzymatic hydrolysis on the cellulose and hemicellulose in order to produce a hydrolysate containing sugars; and fermenting the sugars of the hydrolysate in the presence of a fermenting microorganism in order to produce a biofuel, wherein acetate is coproduced as a byproduct of the process.

* * * * *